United States Patent
Budin et al.

(10) Patent No.: US 6,858,768 B2
(45) Date of Patent: Feb. 22, 2005

(54) OXIDATIVE DEHYDROGENATION OF ALKANES TO OLEFINS USING AN OXIDE SURFACE

(75) Inventors: Lisa M. Budin, Ponca City, OK (US); Larry M. Meyer, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 179 days.

(21) Appl. No.: 10/106,709

(22) Filed: Mar. 26, 2002

(65) Prior Publication Data

US 2003/0040655 A1 Feb. 27, 2003

Related U.S. Application Data

(60) Provisional application No. 60/309,427, filed on Aug. 1, 2001.

(51) Int. Cl.⁷ ................................................. C07C 5/333
(52) U.S. Cl. ....................................... 585/658; 585/661
(58) Field of Search ............................... 585/658, 660, 585/662, 663

(56) References Cited

U.S. PATENT DOCUMENTS

| | | | |
|---|---|---|---|
| 3,972,954 A | | 8/1976 | Bertus .......................... 260/680 |
| 4,255,284 A | * | 3/1981 | Hardman ..................... 502/211 |
| 6,072,097 A | * | 6/2000 | Yokoyama et al. ......... 585/658 |
| 6,235,678 B1 | * | 5/2001 | Mamedov et al. .......... 502/354 |

OTHER PUBLICATIONS

PCT International Search Report for International Application No. PCT/US02/24111 dated Dec. 18, 2002 (2 p.).

* cited by examiner

*Primary Examiner*—Thuan D Dang
(74) *Attorney, Agent, or Firm*—Conley Rose, P.C.

(57) ABSTRACT

A catalyst useful for the production of olefins from alkanes via oxidative dehydrogenation (ODH) is disclosed. The catalyst includes an oxide selected from the group containing alumina, zirconia, titania, yttria, silica, niobia, and vanadia. The catalyst does not contain any unoxidized metals; it is activated by higher preheat temperatures. As a result, similar conversions are achieved at a considerably lower cost.

6 Claims, No Drawings

US 6,858,768 B2

OXIDATIVE DEHYDROGENATION OF ALKANES TO OLEFINS USING AN OXIDE SURFACE

CROSS-REFERENCE TO RELATED APPLICATIONS

The present application claims the benefit of provisional application Ser. No. 60/309,427, filed Aug. 1, 2001 and entitled *Oxidative Dehydrogenation of Alkanes to Olefins Using An Oxide Surface.*

STATEMENT REGARDING FEDERALLY SPONSORED RESEARCH OR DEVELOPMENT

Not Applicable.

TECHNICAL FIELD OF THE INVENTION

This invention generally relates to the conversion of alkanes to alkenes. More specifically, the invention relates to employing oxidative dehydrogenation (ODH) to convert alkanes to alkenes. Still more specifically, the invention relates to non-metal catalysts used in ODH.

BACKGROUND OF THE INVENTION

In the commercial production of plastics, elastomers, man-made fibers, adhesives, and surface coatings, a tremendous variety of polymers are used. There are many ways to classify these compounds. For example, polymers can be categorized according to whether they are formed through chain-growth or step-growth reactions. Alternatively, polymers can be divided between those that are soluble in selective solvents and can be reversibly softened by heat, known as thermoplastics, and those that form three-dimensional networks that are not soluble and cannot be softened by heat without decomposition, known as thermosets. Additionally, polymers can be classified as either made from modified natural compounds or made from entirely synthetic compounds.

A logical way to classify the major commercially employed polymers is to divide them by the composition of their monomers, the chains of linked repeating units that make up the macromolecules. Classified according to composition, industrial polymers are either carbon-chain polymers (also called vinyls) or heterochain polymers (also called noncarbon-chain, or nonvinyls). In carbon-chain polymers, as the name implies, the monomers are composed of linkages between carbon atoms; in heterochain polymers a number of other elements are linked together in the monomers, including oxygen, nitrogen, sulfur, and silicon.

By far the most important industrial polymers are polymerized olefins, which comprise virtually all commodity plastics. Olefins, also called alkenes, are unsaturated hydrocarbons (compounds containing hydrogen [H] and carbon [C]) whose molecules contain one or more pairs of carbon atoms linked together by a double bond. The olefins are classified in either or both of the following ways: (1) as cyclic or acyclic (aliphatic) olefins, in which the double bond is located between carbon atoms forming part of a cyclic (closed-ring) or an open-chain grouping, respectively, and (2) as monoolefins, diolefins, triolefins, etc., in which the number of double bonds per molecule is, respectively, one two, three, or some other number.

Generally, olefin molecules are commonly represented by the chemical formula $CH_2=CHR$, where C is a carbon atom, H is a hydrogen atom, and R is an atom or pendant molecular group of varying composition. The composition and structure of R determines which of the huge array of possible properties will be demonstrated by the polymer.

More specifically, acyclic monoolefins have the general formula $C_nH_{2n}$, where n is an integer. Acyclic monoolefins are rare in nature but are formed in large quantities during the cracking of petroleum oils to gasoline. The lower monoolefins, i.e., ethylene, propylene, and butylene, have become the basis for the extensive petrochemicals industry. Most uses of these compounds involve reactions of the double bonds with other chemical agents. Acyclic diolefins, also known as acyclic dialkenes, or acyclic dienes, with the general formula $C_nH_{2n-2}$, contain two double bonds; they undergo reactions similar to the monoolefins. The best-known dienes are butadiene and isoprene, used in the manufacture of synthetic rubber.

Olefins containing two to four carbon atoms per molecule are gaseous at ordinary temperatures and pressure; those containing five or more carbon atoms are usually liquid at ordinary temperatures. Additionally, olefins are only slightly soluble in water. Olefins have traditionally been produced from alkanes by fluid catalytic cracking (FCC) or steam cracking, depending on the size of the alkanes. Heavy olefins are herein defined as containing at least five carbon atoms and are produced by FCC. Light olefins are defined herein as containing one to four carbon atoms and are produced by steam cracking. Alkanes are similar to alkenes, except that they are saturated hydrocarbons whose molecules contain carbon atoms linked together by single bonds. The simplest alkanes are methane ($CH_4$, the most abundant hydrocarbon), ethane ($CH_3CH_3$), and propane ($CH_3CH_2CH_3$). These three compounds exist in only one structure each. Higher members of the series, beginning with butane ($CH_3CH_2CH_2CH_3$), may be constructed in two or more different ways, depending on whether the carbon chain is straight or branched. Such compounds are called isomers; these are compounds with the same molecular formula but different arrangements of their atoms. As a result, they often have different chemical properties.

In the conversion of alkanes to alkenes, fluid catalytic cracking and steam cracking (direct catalytic dehydrogenation processes) are known to have their drawbacks. For example, the processes are endothermic, meaning that heat is absorbed by the reactions and the temperature of the reaction mixtures decline as the reactions proceed. This is known to lower the product yield, resulting in lower value products. In addition, coke forms on the surface of the catalyst during the cracking processes, covering active sites and deactivating the catalyst. During regeneration, the coke is burned off the catalyst to restore its activity and to provide heat needed to drive the cracking.

This cycle is very stressful for the catalyst; temperatures are high and fluctuate and coke is repeatedly deposited and burned off. Furthermore, the catalyst particles are moving at high speed through steel reactors and pipes, where wall contacts and interparticle contacts are impossible to avoid.

While it may be easy to dismiss catalyst damage and loss in less expensive catalysts, the catalysts used in FCC and steam cracking units are quite expensive. The expense stems from the use of precious metals. For example, a typical supported metal catalyst may cost in the range of $20–$40 per pound, of which the cost of the precious metals may be between 50–80%. Thus, for a reactor that uses 2 million pounds of catalyst, the total cost of the metals in the reactor is considerable. Further, because FCC and steam cracking units are large and require steam input, the overall processes are expensive even before taking catalyst cost into consideration.

As a result, because olefins comprise the most important building blocks in modern petrochemical industry, the development of alternate routes other than FCC and steam reforming have been explored. One such route is oxidative dehydrogenation (ODH). In ODH, an organic compound is dehydrogenated in the presence of oxygen. Oxygen may be fed to the reaction zone as pure oxygen, air, oxygen-enriched air, oxygen mixed with a diluent, and so forth. Oxygen in the desired amount may be added in the feed to the dehydrogenation zone and oxygen may also be added in increments to the dehydrogenation zone. However, catalysts for oxidative dehydrogenation are still being investigated and the development of more effective catalysts for ODH is highly desirable.

SUMMARY OF THE INVENTION

The present invention provides a non-metal catalyst for use in ODH. ODH was chosen for alkane dehydrogenation because it overcomes thermodynamic limitations of olefin yield faced in direct dehydrogenation and rapid coking of the catalysts resulting in short catalyst life.

Although oxidative dehydrogenation usually involves the use of a catalyst, and is therefore literally a catalytic dehydrogenation, oxidative dehydrogenation (ODH) is distinct from what is normally called "catalytic dehydrogenation" in that the former involves the use of an oxidant, and the latter does not. In the disclosure herein, "oxidative dehydrogenation", though employing a catalyst, will be understood as distinct from so-called "catalytic dehydrogenation" processes in that the latter do not involve the interaction of oxygen with the hydrocarbon feed.

In accordance with a preferred embodiment of the present invention, a catalyst for use in ODH processes includes an oxide selected from the group containing alumina, zirconia, titania, yttria, silica, niobia, and vanadia.

In accordance with another preferred embodiment of the present invention, a method for the production of olefins includes contacting a preheated alkane and oxygen stream with a catalyst containing an oxide, sufficient to initiate the oxidative dehydrogenation of the alkane (between 500–700° C.), maintaining a contact time of the alkane with the catalyst for less than 200 milliseconds, and maintaining oxidative dehydrogenation favorable conditions.

In accordance with an alternate preferred embodiment of the present invention, a method for converting alkanes to olefins includes contacting a preheated alkane and oxygen stream with a catalyst containing an oxide, sufficient to initiate the oxidative dehydrogenation of the alkane (between 500–700° C.), maintaining a contact time of the alkane with the catalyst for less than 200 milliseconds, and maintaining oxidative dehydrogenation favorable conditions.

In accordance with yet another preferred embodiment of the present invention, an ODH catalyst includes an oxide selected from the group containing alumina, zirconia, titania, yttria, silica, niobia, and vanadia.

In accordance with still yet another preferred embodiment of the present invention, a disposable ODH catalyst includes an oxide selected from the group containing alumina, zirconia, titania, yttria, silica, niobia, and vanadia.

DETAILED DESCRIPTION OF THE PREFERRED EMBODIMENTS

The present invention relates to a non-metal oxide support for converting alkanes to alkenes via ODH. Typically ODH catalysts contain a precious metal, such as platinum, which promotes alkane conversion. The present invention however, does not contain any unoxidized metals; it is activated by higher preheat temperatures. As a result, similar conversions are achieved at a considerably lower cost.

In a preferred embodiment of the present invention, light alkanes and $O_2$ are converted to the corresponding alkenes employing new oxide catalysts. Preferably, a millisecond contact time syngas reactor is used. Use of a millisecond contact time reactor for the commercial scale conversion of light alkanes to corresponding alkenes will reduce capital investment and increase alkene production significantly. Ethylene yield of 52% or higher is achievable. This technology has the potential of achieving yields above that of the conventional technology at a much lower cost. The need for steam addition, as is currently required in the conventional cracking technology, is eliminated by the present process. However, in some embodiments, the use of steam is preferred. There is minimal coking in the present process and therefore little unit down time and loss of valuable hydrocarbon feedstock. The novel catalysts improve the selectivity of the process to the desired alkene. In addition, the carbon oxide product produced at low levels is preferably primarily CO, not $CO_2$, and is thus more valuable for adjusting the syngas ratio of $H_2/CO$ for possible use in Fischer-Tropsch processes.

The present catalysts are preferably in the form of foam, monolith, gauze, noodles, balls, pills or the like, for operation at the desired high gas velocities with minimal back pressure.

In some embodiments, ODH is carried out using the hydrocarbon feed mixed with an appropriate oxidant and possibly steam. Appropriate oxidants may include, but are not limited to $I_2$, $O_2$, $CO_2$ and $SO_2$. Use of the oxidant shifts the equilibrium of the dehydrogenation reaction towards complete conversion through formation of compounds containing the abstracted hydrogen (e.g. $H_2O$, HI, $H_2S$). Steam, on the other hand, may be used to activate the catalyst, remove coke from the catalyst via a water-gas shift reaction, or serve as a diluent for temperature control.

Catalysts

In the present example, the catalysts were purchased from Porvair Advanced Materials. Commercial products AL and PSZ46 correspond to product compositions $Al_2O_3$ and partially stabilized $ZrO_2$/MgO, respectively. The catalysts tested were in the form of foam monoliths.

Test Procedure and Results

Once the catalysts were purchased, they were calcined at 500° C. and tested in an atmospheric millisecond contact time reactor for 20–30 milliseconds at 900,000 NL/kg/$h^{GHSV}$ with a 10% nitrogen dilution and a molar fuel to oxygen ratio of 1.8. The results can be seen in Table 1 below.

TABLE 1

Test Results for Oxide Supports

| Catalyst | Preheat Temp (° C.) | Ethane Conv. | Selectivity | | | Ethylene Yield | CO Yield | $H_2$ Yield |
|---|---|---|---|---|---|---|---|---|
| | | | Ethylene | CO | $H_2$ | | | |
| AL | 630 | 98.2 | 41.2 | 29.4 | 38.3 | 40.5 | 28.9 | 33.3 |
| AL | 660 | 96.9 | 47.8 | 27.1 | 31.0 | 46.4 | 26.3 | 30.0 |
| PSZ46 | 525 | 94.9 | 55 | 30.2 | 35.2 | 52.2 | 24.1 | 33.4 |

Non-metal oxide supports produce ethylene yields comparable to precious metal-containing oxide supports. While titania, yttria, silica, niobia and vanadia were not tested, it is believed that they will behave similarly to the alumina and zirconia samples. Additionally, because the catalysts do not contain expensive metals components, they will be fairly easy to dispose of.

Process of Producing Olefins

Any suitable reaction regime is applied in order to contact the reactants with the catalyst. One suitable regime is a fixed bed reaction regime, in which the catalyst is retained within a reaction zone in a fixed arrangement. Catalysts may be employed in the fixed bed regime using fixed bed reaction techniques well known in the art. Preferably a millisecond contact time reactor is employed. A general description of major considerations involved in operating a reactor using millisecond contact times is given in U.S. Pat. No. 5,654,491, which is incorporated herein by reference.

Accordingly, a feed stream comprising a hydrocarbon feedstock and an oxygen-containing gas is contacted with one of the above-described non-metal oxide catalysts in a reaction zone maintained at conversion-promoting conditions effective to produce an effluent stream comprising alkenes. The hydrocarbon feedstock may be any gaseous hydrocarbon having a low boiling point, such as ethane, natural gas, associated gas, or other sources of light hydrocarbons having from 1 to 10 carbon atoms. In addition, hydrocarbon feeds including naphtha and similar feeds may be employed. The hydrocarbon feedstock may be a gas arising from naturally occurring reserves of ethane that contain carbon dioxide. Preferably, the feed comprises at least 50% by volume light alkanes ($<C_{10}$).

The hydrocarbon feedstock is contacted with the catalyst as a gaseous phase mixture with an oxygen-containing gas, preferably pure oxygen. The oxygen-containing gas may also comprise steam and/or $CO_2$ in addition to oxygen. Alternatively, the hydrocarbon feedstock is contacted with the catalyst as a mixture with a gas comprising steam and/or $CO_2$.

The process is operated at atmospheric or superatmospheric pressures, the latter being preferred. The pressures may be from about 100 kPa to about 12,500 kPa, preferably from about 130 kPa to about 5,000 kPa. The process of the present invention may be operated at temperatures of from about 400° C. to about 800° C., preferably from about 500° C. to about 700° C. The hydrocarbon feedstock and the oxygen-containing gas are preferably pre-heated before contact with the catalyst. The hydrocarbon feedstock and the oxygen-containing gas are passed over the catalyst at any of a variety of space velocities.

Gas hourly space velocities (GHSV) for the process, stated as normal liters of gas per kilogram of catalyst per hour, are from about 20000 to at least about 100,000,000 NL/kg/h, preferably from about 50,000 to about 50,000,000 NL/kg/h. Preferably the catalyst is employed in a millisecond contact time reactor. The process preferably includes maintaining a catalyst residence time of no more than 200 milliseconds for the reactant gas mixture. Residence time is inversely proportional to space velocity, and high space velocity indicates low residence time on the catalyst. An effluent stream of product gases, including CO, $CO_2$, $H_2$, $H_2O$, and unconverted alkanes emerges from the reactor.

In some embodiments, unconverted alkanes may be separated from the effluent stream of product gases and recycled back into the feed. Product $H_2$ and CO may be recovered and used in other processes such as Fischer-Tropsch synthesis and methanol production.

In some embodiments the use of steam may be employed. As mentioned above, steam may be used to activate the catalyst, remove coke from the catalyst via a water-gas shift reaction (WGS), or serve as a diluent for temperature control.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, the present invention may be incorporated into a gas to liquids plant (GTL) or may stand alone. Accordingly, the scope of protection is not limited by the description set out above, but is only limited by the claims which follow, that scope including all equivalents of the subject matter of the claims. The disclosures of all patents and publications cited herein are incorporated by reference in their entireties.

What is claimed is:

1. A method for the production of olefins by oxidative dehydrogenation wherein the method comprises the steps of:
    (a) forming a feed stream comprising an alkane and an oxidant;
    (b) heating the feed steam to a temperature of approximately 300–700° C.;
    (c) contacting the feed stream with a catalyst consisting essentially of one or more oxides selected from the group containing alumina, zirconia, titania, yttria, silica, niobia, and vanadia;
    (d) maintaining a contact time of the feed stream with said catalyst for less than 200 milliseconds under oxidative dehydrogenation favorable conditions so as to produce olefins; and
    (e) recovering olefins.

2. The method according to claim 1 wherein the oxidant is essentially pure oxygen.

3. The method according to claim 1 wherein the catalyst comprises primarily zirconia.

4. The method according to claim 1 wherein olefin production occurs in a millisecond contact time reactor.

5. The method according to claim 1 wherein the recovered olefins include ethylene and the ethylene yield is at least 25%.

6. The method according to claim 1 wherein the recovered olefins include ethylene and the ethylene yield is at least 50%.

* * * * *